United States Patent [19]

Athey

[11] 4,421,813

[45] Dec. 20, 1983

[54] COVERSTOCK FABRICS

[75] Inventor: Graham Athey, Harrogate, England

[73] Assignee: Imperial Chemical Industries Limited, London, England

[21] Appl. No.: 273,687

[22] Filed: Jun. 15, 1981

[30] Foreign Application Priority Data

Jul. 10, 1980 [GB] United Kingdom ............... 8022562

[51] Int. Cl.³ ............................................. B32B 3/00
[52] U.S. Cl. ................................... 428/195; 428/219; 428/288; 428/296; 428/373
[58] Field of Search ............... 428/195, 198, 219, 288, 428/296, 360, 373

[56] References Cited

U.S. PATENT DOCUMENTS 3,595,731  7/1971  Davies et al. ............... 428/296

FOREIGN PATENT DOCUMENTS 29666  6/1981  European Pat. Off. .

Primary Examiner—James J. Bell
Attorney, Agent, or Firm—Scully, Scott, Murphy & Presser

[57] ABSTRACT

A coverstock fabric comprising an area-bonded nonwoven fabric containing a plurality of homofilament staple fibres and a plurality of heterofilament staple fibres, the fabric having a soak through less than 3.5 seconds, a re-wet moisture less than 0.2 grams and a K factor less than 0.6 and preferably less than 0.4.

6 Claims, 2 Drawing Figures

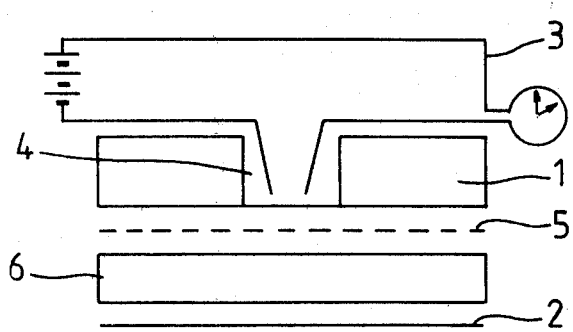

COVERSTOCK FABRICS

This invention relates to a lightweight non-woven fabric for use as a nappy facing material, often referred to as a coverstock fabric.

Traditionally coverstock fabrics have been made from parallel laid viscose rayon non-woven fabrics which have been print bonded using a water-based polyvinyl acetate or polyacrylate emulsion adhesive.

In order to improve the re-wet moisture properties of the coverstock fabric and so improve the baby's comfort, a move away from a hydrophilic rayon fibre to a hydrophobic synthetic fibre such as a polyester or a polyolefin fibre is taking place.

Apart from having a suitable wet strength, such fabrics are required to have acceptable soak through and re-wet moisture properties.

"Soakthrough" is the time in seconds that is needed for 5 ml of simulated urine to pass through a coverstock fabric and be absorbed by the nappy core and determines whether the nappy leaks during urination.

"Re-wet moisture" is the weight in grams of simulated urine that is wicked out of the nappy core and through the coverstock fabric by a standard blotter in 2 minutes and is a measure of how wet the baby's skin would be when it is in contact with a wet nappy.

In general, manufacturers of coverstock fabrics aim for a soakthrough less than 3.5 seconds and a re-wet moisture less than 0.25 grams. With the coverstock fabrics produced hitherto it has been difficult, if not impossible, to comply with these figures and it has been suggested that a re-wet moisture of 0.30 grams could be more realistically achieved.

Surprisingly we have now found that a coverstock fabric can be produced with much improved soak-through and re-wet moisture properties.

According to the invention we provide a coverstock fabric comprising an area-bonded non-woven fabric containing a plurality of homofilament staple fibres and a plurality of heterofilament staple fibres, the fabric having a soakthrough less than 3.5 seconds, a re-wet moisture less than 0.2 grams and a K factor less than 0.6 and preferably less than 0.4.

The term "K factor" as used herein is "soakthrough" × "re-wet moisture" and so combines the two interrelated variable fabric properties.

Particularly desirable fabrics according to the invention are those in which the homofilaments are based on polymers of terephthalic acid, the best known representative being polyethylene terephthalate, and the heterofilaments comprise a core of a polymer based on terephthalic acid, for example polyethylene terephthalate, and a sheath of a polymer such as polyethylene isophthalate/polyethylene terephthalate copolymer.

Nevertheless desirable fabrics can also be produced from other types of homofilaments and heterofilaments including those formed from polyolefin polymers.

We have found that particularly useful coverstock fabrics having adequate tensile strengths coupled with acceptable cost can be produced containing from 75% to 45% of homofilaments of polyethylene terephthalate and containing from 25% to 55% of heterofilaments having a core of polyethylene terephthalate and a sheath of polyethylene isophthalate/polyethylene terephthalate copolymer. We prefer that the staple fibre homofilaments and heterofilaments have a decitex less than 3 and more preferable between 1.5 and 2 in order to obtain optimum cover/re-wet moisture.

Staple fibre blends of such homofilament and heterofilament fibres are conveniently produced by the method described in our copending patent application 7940728.

Blends produced in this way can be readily converted into a non-woven web by a conventional carding process, optionally followed by cross-lapping, or by an air laying process.

The non-woven web is then "area-bonded" by which we mean that the fibres in the web are self-bonded to each other at substantially all crossover points throughout the thickness and over the whole area of the web.

Coverstock fabrics according to the invention may be produced in any suitable weight. However, in general, from a cost point of view the fabrics of the invention will not exceed 30 grams/square meter and will usually be of the order of 25 grams/square meter.

Figure 1:
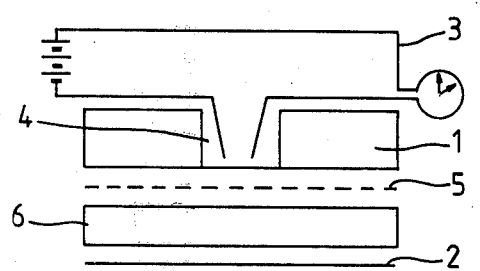
FIG. 1 is a schematic view of the apparatus for measuring soakthrough.

The invention will now be described by way of the following examples:

EXAMPLES 1 to 4 ACCORDING TO INVENTION

A plurality of continuous 67/33 core/sheath heterofilament fibres having a polyethylene terephthalate core and a 15 mole % polyethylene isophthalate/polyethylene terephthalate copolymer sheath were blended with a plurality of continuous homofilaments of polyethylene terephthalate to form a composite tow of filaments.

Various proportions of heterofilament fibres and homofilament fibres were used so that a number of composite tows were produced.

The tows were drawn by the process described in UK Patent No. 1,362,793, with a stuffer box crimping operation and chopped into staple by a Lummus cutter. The staple had a length of 38 mms. The homofilaments were of 2.0 decitex and the heterofilaments were of either 2.0 or 3.3 decitex.

Four samples were produced and labelled 1 to 4. The properties appropriate to each sample are given in Table 1.

TABLE 1

| SAMPLE No | % HETEROFILAMEMT | MEAN DECITEX |
|---|---|---|
| 1 | 26 | 2.0 |
| 2 | 49 | 2.0 |
| 3 | 34 | 2.31 |
| 4 | 48 | 2.53 |

In sample Nos. 1 and 2, the heterofilaments had a decitex of 2.0 and the homofilaments had a decitex of 2.0. In sample Nos. 3 and 4, the heterofilaments had a decitex of 3.3 and the homofilaments a decitex of 2.0.

The four samples were converted into approximately 25 grams/square meter webs by a carding process. The fibre was opened and converted into lap and the lap processed through a randomised card to give a web of approximately 12 grams/square meter. Two webs were laminated together to produce the final fabric. The four webs were area bonded by passing the webs through an Efco oven at a temperature of 225° C. at a speed of 2.0 meters/minute with a 45 second dwell time in the oven.

All four sample webs were subjected to a variety of tests, the results obtained being recorded in Table 2 (MD denoting Machine Direction and CD denoting Cross Direction).

TABLE 2

| TEST | 1 | | 2 | | 3 | | 4 | |
|---|---|---|---|---|---|---|---|---|
| | MD | CD | MD | CD | MD | CD | MD | CD |
| Breaking Load Normalised to 25 gsm (N/5 cm) | | | | | | | | |
| Dry | 13.9 | 6.9 | 26.5 | 15.1 | 17.1 | 9.4 | 22.8 | 15.4 |
| Wet | 10.7 | 6.1 | 23.2 | 13.3 | 14.7 | 7.7 | 19.2 | 13.4 |
| Opacity (%) | 16.5 | | 16.5 | | 17.4 | | 14.0 | |
| Soak through (secs) | 3.1 | | 2.5 | | 3.2 | | 2.8 | |
| Re-wet moisture (gms) in 2 mins | 0.134 | | 0.128 | | 0.113 | | 0.184 | |
| Thickness (mm) | 0.82 | | 0.81 | | 0.94 | | 0.86 | |
| Specific volume (cm³/gm) | 35.4 | | 40.5 | | 37.4 | | 42.4 | |
| K factor | 0.415 | | 0.32 | | 0.41 | | 0.51 | |

COMPARATIVE EXAMPLES 5 to 8

Examples 1 to 4 were repeated up to the stage of preparing webs from the samples of heterofilament-/homofilament staple fibre. The four samples (now referred to as Samples 5 to 8) were converted into approximately 25 grams/square meter webs by a carding process. The fibre was opened and converted into lap and the lap processed through a randomised card to give a web of approximately 12 grams/square meter. Two webs were laminated together to produce the final fabric. The four webs produced were point bonded on a Ramisch Calender. The bottom roll carried a pattern in the form of splines and was at 193° C. The top roll carried a pattern in the form of rings and was at 194° C. The roll pressure was 5 tonnes and roll speed 3 meters/minute. The combination of the two rolls produced a chequeboard pattern giving an area bond of approximately 10%.

All four samples were subjected to a variety of tests, results obtained being recorded in Table 3 (MD denoting machine direction and CD cross direction).

TABLE 3

| TEST | 5 | | 6 | | 7 | | 8 | |
|---|---|---|---|---|---|---|---|---|
| | MD | CD | MD | CD | MD | CD | MD | CD |
| Breaking Load Normalised to 25 gsm (N/5 cm) | | | | | | | | |
| Dry | 22.2 | 8.0 | 30.5 | 13.9 | 14.8 | 5.9 | 21.3 | 11.2 |
| Wet | 15.8 | 6.7 | 25.5 | 11.0 | 11.4 | 4.8 | 16.6 | 8.7 |
| Opacity (%) | 19.3 | | 17.1 | | 18.3 | | 18.0 | |
| Soak through (secs) | 2.1 | | 1.8 | | 2.2 | | 2.2 | |
| Re-wet moisture (gms) in 2 mins | 2.00 | | 1.34 | | 1.40 | | 1.77 | |
| Thickness (mm) | 0.38 | | 0.39 | | 0.39 | | 0.37 | |
| Specific volume (cm³/gm) | 15.5 | | 19.2 | | 18.6 | | 16.6 | |
| K factor | 4.2 | | 2.4 | | 3.08 | | 3.9 | |

It will be noted that sample webs 5 to 8 though having a greater strength than sample webs 1 to 4 and meeting the specified soakthrough requirements for the coverstock fabric do not meet the specified re-wet requirements.

COMPARATIVE EXAMPLE 9

A non-woven web was produced from a 1.5 decitex 38 mm viscose rayon fibre using a conventional carding process. The web was print bonded with 20% (dry weight) polyvinyl acetate adhesive at 130° C. to give a resultant fabric weight of 20 grams per square meter. The bonded web had a soakthrough of 1.06 seconds, a re-wet moisture of 4.22 grams in 2 minutes and a K factor of 4.47.

COMPARATIVE EXAMPLE 10

A non-woven web was produced from a 1.7 decitex 38 mm polyester staple fibre using a conventional carding process. The web was print bonded with 30% (dry weight) polyvinyl acetate adhesive at 130° C. to give a resultant fabric weight of 20 grams per square meter. The bonded web had a soak through of 1.8 seconds, a re-wet moisture of 0.68 grams in 2 minutes and a K factor of 1.22.

The methods of measuring "soakthrough" and "re-wet moisture" as devised by Paper Products International (Reference G - V - P - 2 Issue 4) are now described with reference to the accompanying schematic drawings:

SOAKTHROUGH

In FIG. 1 is shown schematically the apparatus for measuring soakthrough and includes soakthrough plate 1 (Paper Products A - PP - 562), an impervious base plate 2 (Paper Products 4A - PP - 271) and an electrical timing circuit 3 wired to probes on the soakthrough plate. The soakthrough plate includes a cavity 4 into which a liquid sample can be discharged. Also shown is a specimen coverstock fabric 5 under test and an absorbent core 6 (Eaton-Dikeman Co. No 939).

A test solution simulating urine having a surface tension of 45 dynes/cm was prepared as follows:

Using a torsion balance (500 gram capacity, 0.005 gram sensitivity), 1.0±0.01 grams of a surfactant - Triton X-100 (available from Paper Products) was weighed into a clean, dry 100 ml volumetric flask. This was diluted to volume with distilled water. A magnetic stirring bar was inserted in the flask which was then placed on a stirring motor. The solution was stirred for approximately 5 minutes to form the base solution.

Using a torsion balance (500 gram capacity, 0.005 gram sensitivity), 20.0±0.01 grams of sodium chloride were weighed and transferred to a 2000 ml volumetric flask. 5.0+0.01 grams of the base solution were added and diluted to volume with distilled water. A magnetic stirring bar was inserted in the flask which was placed on a stirring motor. The solution was stirred for approximately 5 minutes to form the test solution. The surface tension of the test solution was measured. If the test solution was found to have a surface tension outside 45±3 dynes it was either adjusted carefully with base solution or distilled water or it was discarded and a fresh solution prepared. The soakthrough of the test solution through the coverstock fabric under test was then measureed in a room maintained at 73° F. at a relative humidity of 50% as follows.

Three cores were prepared by cutting nine - 101.6 mm × 101.6 mm squares of Eaton-Dikeman No 939 filter paper using three superimposed squares to make each core. Condition the cores for at least 24 hours at 73° F./50% relative humidity Cut three - 125 mm × 125 mm squares of the specimen coverstock fabric and condition for at least 2 hours at 73° F./50% relative humidity.

Set up a ring stand for a separatory funnel so that the tip of the funnel is about two inches above the base of the ring stand.

(The separatory funnel was a Matheson 25356-15 or equivalent provided with a Teflon stopcock having a capacity of 125 mls and which allows a rate of discharge of 25.0 mls in 3.5±0.25 seconds. The stem of the funnel was cut off at a right angle about one inch below the stopcock. If necessary the rate of discharge from the separatory funnel could be increased by enlarging the bore of the hole in the stopcock with a small drill).

A clean burette (50 mls, Matheson 6130-70 or equivalent) was set up so that the tip of the burette was inside the separatory funnel. The burette was filled with the test solution to the zero mark making sure that the burette tip was also filled.

A conditioned core was placed on the base plate and a conditioned square of the coverstock fabric placed on top of the core and lightly pressed against it. The soakthrough plate was centred on the exposed surface of the coverstock fabric and the assembly centred under the stem of the funnel with the tip of the funnel ¼±1/32 inch above the top of the soakthrough plate.

With the separatory funnel stopcock closed, 5.0 mls of the test solution were discharged from the burette into the separatory funnel. With the timer power ON, the timer set to zero, and the probes in the soakthrough cavity, a soakthrough test was started by opening the funnel stopcock and discharging the 5.0 mls into the plate cavity. The initial liquid started the timer and after the liquid emptied from the cavity, the timer stops. The soakthrough time was recorded to the nearest 0.1 second.

RE-WET MOISTURE

Figure 2:
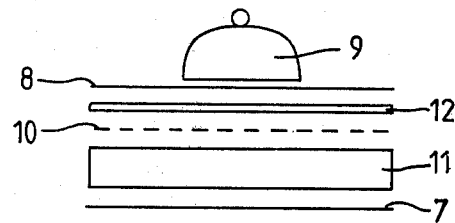
FIG. 2 is a schematic view of the apparatus for measuring re-wet moisture.

In FIG. 2 is shown schematically the apparatus for measuring re-wet moisture and includes an impervious base plate 7, impervious pressure plate 8 provided, on its underside, with a layer of foam and, on its upper side, with a compression weight 9. The total weight of items 8 and 9 was 3.63 Kgs. Both items are available through Paper Products Engineering Services.

Also shown in a specimen coverstock fabric 10, an absorbent core 11 as used in the soakthrough test, and a two ply filter paper 12.

Immediately after completing the soakthrough test, and with the separatory stopcock closed, the remaining amount of test solution (core loading minus 5.0 mls—see below) was discharged into the funnel. The stopcock was opened and the solution discharged into the sample, care being taken not to overflow the plate cavity.

(Core loading is calculated by multiplying the weight of the core, i.e. 3- 101.6 mm × 101.6 mm squares of Eaton-Dikeman No 939 filter paper, by 3.8. For example if the core weight is 4.35 grams then the core loading, i.e. total volume of test solution required to load core, is 4.35 × 3.8 = 16.5 mls.)

Immediately after the core was fully loaded with the test solution (determined by visual inspection) the burette, funnel and soakthrough plate were removed.

The pressure plate, and compression weight, were centred, with the foam side down, over the top of the coverstock fabric. A stopwatch was started immediately.

After exactly 3.0 minutes, the stopwatch was stopped and reset to zero. The pressure plate and compression weight were quickly removed and the plate wiped dry.

Centre two pieces of filter paper (15 cm diameter Whatman Inc No 4), which had previously been conditioned for at least 24 hours at 73° F./50% relative humidity, over the coverstock fabric. The pressure plate and compression weight were carefully and slowly replaced over the assembly (see FIG. 2).

The stopwatch was started. After exactly 2.0 minutes the filter papers were removed and weighed to the nearest 0.01 gram. The re-wet moisture weight which was the difference in weight between the wet and dry filter papers was recorded.

Both tests were repeated with the remaining samples and the average soakthrough and re-wet moisture calculated.

I claim:

1. A coverstock fabric comprising an area-bonded non-woven fabric containing a plurality of homofilament staple fibres comprising polyethylene terephthalate and a plurality of heterofilament staple fibres comprising a core of polyethylene terephthalate and a sheath of polyethylene isophthalate/polyethylene terephthalate copolymer, the fabric having a soakthrough less than 3.5 seconds, a re-wet moisture less than 0.2 grams and a K factor less than 0.6.

2. A coverstock fabric as claimed in claim 1 having a K factor less than 0.4.

3. A coverstock fabric as claimed in claim 1 containing from 75% to 45% of the homofilament staple fibres and from 25% to 55% of the heterofilament staple fibres.

4. A coverstock fabric as claimed in claim 1 in which both the homofilament staple fibres and the heterofilament staple fibres have a decitex less than 3.

5. A coverstock fabric as claimed in claim 4 in which both the homofilament staple fibres and the heterofilament staple fibres have a decitex of between 1.5 and 2.

6. A coverstock fabric as claimed in claim 1 having a weight/area ratio not exceeding 30 grams/square meter.

* * * * *